(12) United States Patent
Singh et al.

(10) Patent No.: US 7,811,611 B2
(45) Date of Patent: Oct. 12, 2010

(54) HERBAL CONTRACEPTIVE FORMULATION

(76) Inventors: Kamalinder Kaur Singh, 103, Belscot Building, Lokhandwala Complex, opp Kamat's Unit, Mumbai, Maharashtra (IN) 400053; Pratima Arun Tatke, a-6, Vaibhar, The Law CHS, Plot No. 12-13, Shaptrinagar, Santacru 2 (West), Mumbai, Maharashtra (IN) 400054; Shruti Dhuru, 2, Aradha,a, Veer Savankai Rd., Mahim, Mumbai, Maharashtra (IN) 4000016

( * ) Notice: Subject to any disclaimer, the term of this patent is extended or adjusted under 35 U.S.C. 154(b) by 0 days.

(21) Appl. No.: 11/884,677

(22) PCT Filed: Jan. 19, 2006

(86) PCT No.: PCT/IN2006/000017

§ 371 (c)(1),
(2), (4) Date: Aug. 20, 2007

(87) PCT Pub. No.: WO2006/087733

PCT Pub. Date: Aug. 24, 2006

(65) Prior Publication Data

US 2008/0152713 A1 Jun. 26, 2008

(30) Foreign Application Priority Data

Jan. 19, 2005 (IN) .......................... 58/MUM/2005

(51) Int. Cl.
*A01N 65/00* (2009.01)
(52) U.S. Cl. ..................................... 424/725
(58) Field of Classification Search ....................... None
See application file for complete search history.

(56) References Cited

U.S. PATENT DOCUMENTS 5,955,497 A * 9/1999 McLaughlin et al. ........ 514/473
2007/0218041 A1* 9/2007 Lu et al. .................... 424/93.7

FOREIGN PATENT DOCUMENTS

JP         2004292778 A    * 10/2004

\* cited by examiner

*Primary Examiner*—Michael V Meller
(74) *Attorney, Agent, or Firm*—Bio Intellectual Property Services LLC; O. M. (Sam) Zaghmout

(57) ABSTRACT

Disclosed herein are non-synthetic herbal based anti-fertility compositions having high spermicidal activity for intravaginal administration comprising hydroalcoholic extract of *Annona squamosa* and pharmaceutically acceptable excipients, in suitably formulated dosage forms for intravaginal administration and a method of contraception in a female subject to prevent pregnancy.

9 Claims, No Drawings

HERBAL CONTRACEPTIVE FORMULATION

FIELD OF INVENTION

The present invention relates to herbal, non-synthetic, Annona squamosa based intravaginal contraceptive formulations having high spermicidal activity. More particularly the present invention relates to intravaginal contraceptive gels and fast disintegrating vaginal contraceptive tablets, free from any synthetic hormonal agents. The present invention further relates to process for preparation of said formulations and to a method for contraception in female subject to prevent pregnancy.

BACKGROUND AND PRIOR ART

In today's context, the problem of over population and the resulting need for birth control are becoming very important. Contraceptives have proved their worth to some extent to control this menace. The methods adopted for birth control, which hinder the occurrence of undesirable pregnancy, include the use of condoms, insertion of intrauterine devices, oral contraceptive pills or use of vaginal preparations such as pessaries, gels, foams, creams etc.

All the known methods above however, having certain disadvantages. Among the above said methods the condoms and vaginal pessary causes, uncomfortable feeling in certain cases. Intrauterine devices are free from these disadvantages but, they have to be inserted only by the physician and also give discomfort during intercourse.

The synthetic contraceptive agents available today for fertility control produce severe side effects such as hormonal imbalance, hypertension, increased risk of cancer, weight gain etc. Hence there is a need to replace these agents by safe and effective non-synthetic agents such as plant based contraceptive agents.

There are many plants with reported anti fertility properties in folklore and traditional medicines. Many plants with anti-fertility activity are known but suitable formulations containing these plants are not available till today. Development of herbal contraceptive drug delivery systems will combine the knowledge of the ancient system of medicine 'Ayurveda' and the modern pharmaceutical technologies available today. The development of plant-based anti fertility drug delivery system will provide a user friendly, safe, effective, stable and cost effective herbal formulation that can be used for population control.

Annona squamosa, Family Annonaceae, is grown to a small extent in Assam and is occasionally found in South India. Seeds of Annona squamosa are emetic, astringent, used as a fish poison and are also insecticidal. They possess anti-implantation activity. 50% ethanolic extract of the seeds was found to possess anti-implantation activity after oral administration in rats (Mishra et al, 1979). Crude seed extract of Annona squamosa showed significant growth inhibitory effects on larva of Spodoptera litura (Audrey Leatemia et al, 2001). Anti-head lice activity of a preparation of Annona squamosa seed extract is reported (Ch. Tiangda et al, 1999).

U.S. Pat. No. 4,762,716 describes the process for extraction of pure annonin from the comminuted seeds of Annona squamosa and its use as insecticide.

CN1319424 discloses ethanolic extract of Annona squamosa root bark or tree bark or branch, leaf or seed or their mixture posses' high anticancer activity and low toxicity. However, the spermicidal activity of the extract from the seeds of Annona squamosa has not been so far investigated.

The present invention provides contraceptive gel formulations and dispersible vaginal tablets which comprises effective amount of hydroalcoholic extract from seeds of Annona squamosa along with other suitable pharmaceutically acceptable excipients. Spermicidal activity of the prepared hydroalcoholic extract of the seeds of Annona squamosa was carried out by the inventors of the present invention.

Intravaginal gels have the advantage of being non-irritant, water miscible, water washable, easily spreadable, compatible with the aqueous vaginal environment and miscible with the vaginal fluid. The method employs applying effective amount of hydro alcoholic extract from the seed of Annona squamosa in gel composition in the vagina to prevent conception.

Vaginal tablets are solid dosage forms for vaginal administration. They offer easy placement in the vagina by means of a plastic inserter. They are less messy and easy to handle. Conventional vaginal tablets disintegrate slowly in the vagina and would not be suitable for incorporation of spermicidal agents, which require faster action. However, our present invention deals with fast disintegrating, non-messy, vaginal tablets for spermicidal activity. The method employs inserting fast disintegrating tablets comprising effective amount of hydro alcoholic extract from the seeds of Annona squamosa to prevent conception.

OBJECTIVE OF THE PRESENT INVENTION

It is an objective of the present invention in its preferred form to provide improved non-synthetic Annona squamosa based contraceptive formulations, which eliminates the disadvantages of the known contraceptives.

It is another objective of the present invention is to provide intravaginal mucoadhesive gel formulations with spermicidal activity, better stability, compatible with the aqueous vaginal environment and miscible with the vaginal fluid.

Yet, another objective of the present invention is to provide fast disintegrating, non-messy vaginal tablets for spermicidal activity.

Still another objective of the invention is to provide a method for contraception in female subjects to prevent pregnancy.

SUMMARY OF THE PRESENT INVENTION

The present invention discloses non-synthetic Annona squamosa based contraceptive formulations having high spermicidal activity, in the form of intra vaginal gel and fast disintegrating contraceptive vaginal tablets being free from hormones. The present invention also discloses the process for preparation of said formulations. The present invention further discloses a method for contraception in female subject to prevent pregnancy.

DETAILED DESCRIPTION OF THE INVENTION

The present invention describes nonsynthetic Annona squamosa based intravaginal contraceptive gels and intravaginal dispersible tablets with high spermicidal activity and process for preparation of said formulations. The present invention further describes a method for contraception in female subject to prevent pregnancy.

In one embodiment there is provided intravaginal gel formulation comprising hydroalcoholic extract from the seeds of Annona squamosa, gelling agents such as Carbopol, Polycarbophil, Lutrol, HPMC, xanthan gum, Pemulen and water, preservative and sodium hydroxide solution. The gel formulation of the present invention can also be used as lubricant in male and female condoms.

Process for the formulation of intravaginal gels:

Carbopol, Polycarbophil, Lutrol F127, HPMC, xanthan gum and Pemulen were soaked separately overnight in water. The hydroalcoholic extract from the seeds of *Annona squamosa* was prepared in the following manner:

Annona fruits were procured from the local market. The seeds were shade dried and then powdered. The powder was then used for extraction. Soxhlet extraction of the powdered seeds was carried out for 48 hrs with 50% alcohol and the extract thus obtained was then evaporated. It was then added to the already soaked gelling agents. The gel containing Carbopol, Polycarbophil and Pemulen was neutralized using 10% NaOH.

The above gels were evaluated separately for pH, water washability, spreadability, mucoadhesion, HPTLC fingerprinting, in vitro and in vivo spermicidal activity. Spermicidal activity of the prepared hydroalcoholic extract from the seeds of *Annona squamosa* was also determined.

Pharmaceutically acceptable excipients used in the gel formulations are selected from gelling agents and thickeners and more specifically from Carbopol940, Carbopol 971, Carbopol 934P, polycarbophil, xanthan gum, HPMC, sodium CMC, Lutrol, carragenan, Pemulen and pectin.

Various formulations are prepared comprising the hydroalcoholic seed extract of *Annona squamosa* varying from 1% to 80%; Carbopol 0.5 to 5%; Polycarbophil 0.5 to 5%; Lutrol 5% to 30%; HPMC 1% to 5%, xanthan gum 0.5 to 5% Pemulen 0.5% to 5% and combinations thereof; preservatives such as propyl paraben, methyl paraben, sodium benzoate, benzalkonium chloride were used in concentration range of 0.01-0.5% to stabilize the gels, evaluate the efficacy; illustrating the invention as follows.

EXAMPLE 1

| | |
|---|---|
| Hydroalcoholic extract of the seeds of *Annona squamosa* | 1% |
| Carbopol 940NF | 0.5% |
| Water | q.s. |
| Preservative | q.s. |
| 10% NaOH | q.s. |

EXAMPLE 2

| | |
|---|---|
| Hydroalcoholic extract of the seeds of *Annona squamosa* | 1% |
| Carbopol 940 NF | 1% |
| Water | q.s. |
| Preservative | q.s. |
| 10% NaOH | q.s. |

EXAMPLE 3

| | |
|---|---|
| Hydroalcoholic extract of the seeds of *Annona squamosa* | 2% |
| Carbopol 940NF | 1% |
| Water | q.s. |
| Preservative | q.s. |
| 10% NaOH | q.s. |

EXAMPLE 4

| | |
|---|---|
| Hydroalcoholic extract of the seeds of *Annona squamosa* | 5% |
| Carbopol 940 NF | 1% |
| Water | q.s. |
| 10% NaOH | q.s. |

EXAMPLE 5

| | |
|---|---|
| Hydroalcoholic extract of the seeds of *Annona squamosa* | 5% |
| Carbopol 940 NF | 1.5% |
| Water | q.s. |
| Preservative | q.s. |
| 10% NaOH | q.s. |

EXAMPLE 6

| | |
|---|---|
| Hydroalcoholic extract of the seeds of *Annona squamosa* | 10% |
| Carbopol 940NF | 1% |
| Water | q.s. |
| 10% NaOH | q.s. |

EXAMPLE 7

| | |
|---|---|
| Hydroalcoholic extract of the seeds of *Annona squamosa* | 10% |
| Carbopol 940 NF | 1.5% |
| Water | q.s. |
| 10% NaOH | q.s. |

EXAMPLE 8

| | |
|---|---|
| Hydroalcoholic extract of the seeds of *Annona squamosa* | 10% |
| Carbopol 934P | 1% |
| Water | q.s. |
| 10% NaOH | q.s. |

EXAMPLE 9

| | |
|---|---|
| Hydroalcoholic extract of the seeds of *Annona squamosa* | 10% |
| Carbopol 934P | 2% |
| Water | q.s. |
| 10% NaOH | q.s. |

EXAMPLE 10

| | |
|---|---|
| Hydroalcoholic extract of the seeds of *Annona squamosa* | 10% |
| Carbopol 934P | 3% |
| Water | q.s. |
| Preservative | q.s. |
| 10% NaOH | q.s. |

EXAMPLE 11

| | |
|---|---|
| Hydroalcoholic extract of the seeds of *Annona squamosa* | 10% |
| Carbopol 934P | 4% |
| Water | q.s. |
| Preservative | q.s. |
| 10% NaOH | q.s. |

EXAMPLE 12

| | |
|---|---|
| Hydroalcoholic extract of the seeds of *Annona squamosa* | 10% |
| Carbopol 934P | 5% |
| Water | q.s. |
| Preservative | q.s. |
| 10% NaOH | q.s. |

EXAMPLE 13

| | |
|---|---|
| Hydroalcoholic extract of the seeds of *Annona squamosa* | 10% |
| Lutrol F127 | 15% |
| Preservative | q.s. |
| Water | q.s. |

EXAMPLE 14

| | |
|---|---|
| Hydroalcoholic extract of the seeds of *Annona squamosa* | 10% |
| Lutrol F127 | 20% |
| Preservative | q.s. |
| Water | q.s. |

EXAMPLE 15

| | |
|---|---|
| Hydroalcoholic extract of the seeds of *Annona squamosa* | 10% |
| Lutrol F127 | 10% |
| Preservative | q.s. |
| Water | q.s. |

EXAMPLE 16

| | |
|---|---|
| Hydroalcoholic extract of the seeds of *Annona squamosa* | 10% |
| Lutrol F127 | 25% |
| Preservative | q.s. |
| Water | q.s. |

EXAMPLE 17

| | |
|---|---|
| Hydroalcoholic extract of the seeds of *Annona squamosa* | 10% |
| HPMC | 3% |
| Preservative | q.s. |
| Water | q.s. |

EXAMPLE 18

| | |
|---|---|
| Hydroalcoholic extract of the seeds of *Annona squamosa* | 10% |
| HPMC | 5% |
| Preservative | q.s. |
| Water | q.s. |

EXAMPLE 19

| | |
|---|---|
| Hydroalcoholic extract of the seeds of *Annona squamosa* | 10% |
| Xanthan gum | 0.5% |
| Preservative | q.s |
| Water | q.s. |

EXAMPLE 20

| | |
|---|---|
| Hydroalcoholic extract of the seeds of *Annona squamosa* | 10% |
| Xanthan gum | 1% |
| Preservative | q.s |
| Water | q.s. |

EXAMPLE 21

| | |
|---|---|
| Hydroalcoholic extract of the seeds of *Annona squamosa* | 10% |
| Xanthan gum | 1.5% |
| Preservative | q.s. |
| Water | q.s. |

EXAMPLE 22

| | |
|---|---|
| Hydroalcoholic extract of the seeds of *Annona squamosa* | 10% |
| Xanthan gum | 2% |
| Preservative | 0.2% |
| Water | q.s. |

EXAMPLE 23

| | |
|---|---|
| Hydroalcoholic extract of the seeds of *Annona squamosa* | 10% |
| Pemulen | 1% |
| Preservative | q.s. |
| Water | q.s. |

EXAMPLE 24

| Hydroalcoholic extract of the seeds of *Annona squamosa* | 10% |
| --- | --- |
| Polycarbophil | 0.5% |
| Preservative | q.s. |
| Water | q.s. |

EXAMPLE 25

| Hydroalcoholic extract of the seeds of *Annona squamosa* | 10% |
| --- | --- |
| Polycarbophil | 0.75% |
| Preservative | q.s. |
| Water | q.s. |

EXAMPLE 26

| Hydroalcoholic extract of the seeds of *Annona squamosa* | 10% |
| --- | --- |
| Polycarbophil | 1% |
| Water | q.s. |
| 10% NaOH | q.s. |
| Preservative | 0.2% |

The following in vitro tests were performed with the gel formulations of the present invention:

pH: The pH of the gels was found to be in the range of 4.5-5.5 compatible with the vaginal pH.

Washability: The gels were readily water washable.

Spreadability: The spreadability of the gels was found to be in the range of 1.58-1.60 seconds.

Mucoadhesion: The mucoadhesive force required ranged from 3.60-8.66 gms

HPTLC Fingerprinting:

The HPTLC fingerprinting of the hydroalcoholic extract of seeds of *Annona squamosa* in ethanol was carried out using solvent system chloroform: acetone (1:1) on High Performance Thin Layer Chromatograph, Linomat IV, Camag Scanner III The HPTLC fingerprint showed 8 peaks with Rf values of 0.01, 0.07, 0.13, 0.29, 0.41, 0.57, 0.75, 0.91 and the HPTLC finger print of vaginal gels matched with that of the extract.

Spermicidal Activity:

Spermicidal activity of the prepared hydroalcoholic extract from the seeds of *Annona squamosa* was also determined using the in vitro, Sander Crammer Immobilization test for determining the spermicidal activity.

Semen samples of healthy male volunteers were used for the study. The samples of motility more than 80% were used for the study. 10 µl of sperm suspension and 10 µl of the hydroalcoholic extract from the seeds of *Annona squamosa* (1:1) were placed on a glass slide. Then it was mixed uniformly and examined under binocular microscope at a magnification of 10×. With the help of stopwatch, the time for the cessation of motility of spermatozoa was studied. The motility of the sperms was observed at different time intervals.

The spermicidal effect was observed 10-15 seconds after mixing.

Spermicidal activity of the formulations was carried out using the in vitro, Sander Crammer Immobilization test for determining the spermicidal activity.

Semen samples of healthy male volunteers were used for the study. The samples of motility more than 80% were used for the study. 10 µl of sperm suspension and 10 µl of the gels (1:1) were placed on a glass slide. Then it was mixed uniformly and examined under binocular microscope at a magnification of 10×. With the help of stopwatch, the time for the cessation of motility of spermatozoa was studied. The motility of the sperms was observed at different time intervals.

Spermicidal effect was found in the range of 20 seconds to 5 minutes.

In Vivo Studies of Vaginal Gels:

In vivo studies of the selected vaginal gel formulations were carried out using rats and rabbits as the animal models.

a) In vivo studies in rats

Evaluation of antifertilty activity of vaginal gels in rats:
  The estrus cycle of the female rats was monitored.
  The estrous cycle of a female rat consists of the following stages:

Proestrous, Estrous, Metestrous and Diestrous
  The animals were weighed and the vaginal smears were prepared and the female reproductive cycle was monitored early in the morning, seven days a week.
  Few drops of saline were taken into a dropper; inserted it into the vagina, taking care not to touch the cervix.
  Saline was expelled into the vagina and withdrawn two or three times.
  The contents of the dropper were placed on a microscope slide.
  The cells (epithelial, cornified, leukocyte) of the smear were observed using a microscope and the estrous cycle of the female rat was determined.

The estrous cycle of the female rat was followed at least for two cycles before including the animal in the test group.

The vaginal gels were administered intravaginally on the evening between the proestrous stage and the estrous stage, the female rats were kept for mating with the male rats since mating normally occurs on the night between the days of proestrous and estrous. The females were then isolated the next morning.

The female rats were then observed for pregnancy and number of litters after 21 days.

The animals mated after administration of the vaginal gels. None of the female rats which were administered Annona vaginal gels delivered while all rats which received the placebo gels delivered pups. Thus Annona vaginal gels showed 100% anti-fertility effect in vivo in rats.

b) Evaluation of antifertilty activity of vaginal gels in rabbits:
  The selected vaginal gels were administered intravaginally to the female rabbits.
  The females were allowed to mate with the male.
  The females were then isolated.
  The number of pregnancies after a period of one month were recorded.

The animals mated immediately after administration of the vaginal gels. None of the female rabbits which were administered Annona vaginal gels delivered while all rabbits which received the placebo gels delivered pups. Thus Annona vaginal gels showed 100% anti-fertility effect in vivo in rabbits.

In another embodiment of the invention, there is provided dispersible fast disintegrating, non-messy, intravaginal tablets for spermicidal activity. The said tablets comprising the hydroalcoholic extract from the seeds of *Annona squamosa* 1 to 80%, along with other suitable pharmaceutically acceptable excipients such as binders, fillers, lubricants, super disintegrants, and diluents in the range of 20-99%.

The pharmaceutically acceptable excipients are selected from lactose, Aerosil, starch, micro crystalline cellulose, mannitol, dicalcium phosphate, dextrose, hydrolysed starch, cellulose derivatives, gelatin, polyvinyl pyrrolidone, starch paste, pregelatinized starch, sodium alginate, sorbitol, clays, cross liked PVP, stearic acid, talc, polyethelene glycol, surfactants, waxes and silica derivatives.

The fillers are selected from the group of lactose, microcrystalline cellulose, dextrose, mannitol, dicalcium phosphate, sorbitol, calcium carbonate, magnesium carbonate, magnesium oxide, Aerosil and the like in the range 20-99%.

The binders are selected from the group of starch, polyvinyl pyrrolidone, sodium alginate, methyl cellulose, ethyl cellulose, pregelatinized starch, gelatin and the like in the range 0.5-10%.

The lubricants are selected from the group of stearic acid, talc, Magnesium stearate, Aerosil, polyethylene glycol and the like in the range 0.5-5%.

The disintegrants are selected from the group of crosspovidone, crosscarmellose sodium, sodium starch glycolate, microcrystalline cellulose, starch, cross linked PVP and the like in the range 1-20%.

The method employs applying effective amount of the hydroalcoholic extract from the seeds of *Annona squamosa* in composition in the vagina to prevent conception.

Process for preparation of fast disintegrating contraceptive vaginal tablets:

The tablets are prepared in such a way that hydroalcoholic extract from the seed of *Annona squamosa* was adsorbed onto Aerosil. Lactose and superdisintegrants are added to it and mixed thoroughly. Granulation was done using PVP in alcohol till dough was obtained. The dough was passed through sieve number 10. The granules were then dried at 100° C. for 3 hours. The dried granules were then passed through sieve number 16. To these granules, weighed amount of magnesium stearate was added. Talc was incorporated, mixed thoroughly and the said blend was punched in a single punch machine.

The granules were evaluated for their bulk density, tapped density and angle of repose.

The tablets were evaluated for uniformity of weight, hardness, disintegration time, friability and spermicidal activity. Tablets were prepared according to the process described above using the following compositions. The invention is illustrated with the following examples.

EXAMPLE 24

| | |
|---|---|
| Hydroalcoholic extract of the seeds of *Annona squamosa* | 10% |
| Aerosil | 40% |
| Lactose | 46% |
| Sodium starch glycolate | 2% |
| 5% Polyvinylpyrrolidone in alcohol | q.s. |
| Talc | 1% |
| Magnesium stearate | 1% |

EXAMPLE 25

| | |
|---|---|
| Hydroalcoholic extract of the seeds of *Annona squamosa* | 15% |
| Aerosil | 40% |
| Lactose | 35% |
| Sodium starch glycolate | 8% |
| 5% Polyvinylpyrrolidone in alcohol | q.s. |
| Talc | 1.0% |
| Magnesium stearate | 1.0% |

EXAMPLE 26

| | |
|---|---|
| Hydroalcoholic extract of the seeds of *Annona squamosa* | 20% |
| Aerosil | 40% |
| Lactose | 30% |
| Sodium starch glycolate | 8% |
| 5% Polyvinylpyrrolidone in alcohol | q.s. |
| Talc | 1.0% |
| Magnesium stearate | 1.0% |

EXAMPLE 27

| | |
|---|---|
| Hydroalcoholic extract of the seeds of *Annona squamosa* | 10% |
| Aerosil | 40% |
| Lactose | 44% |
| Sodium starch glycolate | 4% |
| 5% Polyvinylpyrrolidone in alcohol | q.s. |
| Talc | 1% |
| Magnesium stearate | 1% |

EXAMPLE 28

| | |
|---|---|
| Hydroalcoholic extract of the seeds of *Annona squamosa* | 10% |
| Aerosil | 35% |
| Lactose | 45% |
| Sodium starch glycolate | 8% |
| 5% Polyvinylpyrrolidone in alcohol | q.s. |
| Talc | 1% |
| Magnesium stearate | 1% |

EXAMPLE 29

| | |
|---|---|
| Hydroalcoholic extract of the seeds of *Annona squamosa* | 10% |
| Aerosil | 40% |
| Lactose | 45% |
| Crosspovidone | 3% |
| 5% Polyvinylpyrrolidone in alcohol | q.s. |
| Talc | 1% |
| Magnesium stearate | 1% |

EXAMPLE 30

| | |
|---|---|
| Hydroalcoholic extract of the seeds of *Annona squamosa* | 10% |
| Aerosil | 40% |
| Lactose | 44% |
| Crosspovidone | 4% |
| 5% Polyvinylpyrrolidone in alcohol | q.s. |
| Talc | 1% |
| Magnesium stearate | 1% |

EXAMPLE 31

| | |
|---|---|
| Hydroalcoholic extract of the seeds of *Annona squamosa* | 10% |
| Aerosil | 40% |
| Lactose | 43% |
| Crosspovidone | 5% |
| 5% Polyvinylpyrrolidone in alcohol | q.s. |
| Talc | 1% |
| Magnesium stearate | 1% |

EXAMPLE 32

| | |
|---|---|
| Hydroalcoholic extract of the seeds of *Annona squamosa* | 10% |
| Aerosil | 40% |
| Lactose | 47% |
| Crosscarmellose sodium | 1% |
| 5% Polyvinylpyrrolidone in alcohol | q.s. |
| Talc | 1% |
| Magnesium stearate | 1% |

EXAMPLE 33

| | |
|---|---|
| Hydroalcoholic extract of the seeds of *Annona squamosa* | 10% |
| Aerosil | 40% |
| Lactose | 45% |
| Crosscarmellose sodium | 3% |
| 5% Polyvinylpyrrolidone in alcohol | q.s. |
| Talc | 1% |
| Magnesium stearate | 1% |

EXAMPLE 34

| | |
|---|---|
| Hydroalcoholic extract of the seeds of *Annona squamosa* | 10% |
| Aerosil | 40% |
| Lactose | 43% |
| Crosscarmellose sodium | 5% |
| 5% Polyvinylpyrrolidone in alcohol | q.s. |
| Talc | 1% |
| Magnesium stearate | 1% |

EXAMPLE 35

| | |
|---|---|
| Hydroalcoholic extract of the seeds of *Annona squamosa* | 12.5% |
| Aerosil | 50% |
| Lactose | 25% |
| Sodium Starch Glycolate | 10% |
| 5% Polyvinylpyrrolidone in alcohol | q.s. |
| Talc | 1.25% |
| Magnesium stearate | 1.25% |

EXAMPLE 36

| | |
|---|---|
| Hydroalcoholic extract of the seeds of *Annona squamosa* | 11.76% |
| Aerosil | 47.05% |
| Lactose | 29.41% |
| Sodium Starch Glycolate | 9.41% |
| 5% Polyvinylpyrrolidone in alcohol | q.s. |
| Talc | 1.176% |
| Magnesium stearate | 1.176% |

EXAMPLE 37

| | |
|---|---|
| Hydroalcoholic extract of the seeds of *Annona squamosa* | 11.11% |
| Aerosil | 44.44% |
| Lactose | 33.33% |
| Sodium Starch Glycolate | 8.88% |
| 5% Polyvinylpyrrolidone in alcohol | q.s. |
| Talc | 1.11% |
| Magnesium stearate | 1.11% |

EXAMPLE 38

| | |
|---|---|
| Hydroalcoholic extract of the seeds of *Annona squamosa* | 10.52% |
| Aerosil | 42.10% |
| Lactose | 36.84% |
| Sodium Starch Glycolate | 8.42% |
| 5% Polyvinylpyrrolidone in alcohol | q.s. |
| Talc | 1.05% |
| Magnesium stearate | 1.05% |

EXAMPLE 39

| | |
|---|---|
| Hydroalcoholic extract of the seeds of *Annona squamosa* | 12.5% |
| Aerosil | 43.75% |
| Lactose | 31.25% |
| Sodium Starch Glycolate | 10% |
| 5% Polyvinylpyrrolidone in alcohol | q.s. |
| Talc | 1.25% |
| Magnesium stearate | 1.25% |

EXAMPLE 40

| | |
|---|---|
| Hydroalcoholic extract of the seeds of *Annona squamosa* | 11.76% |
| Aerosil | 41.17% |
| Lactose | 35.29% |
| Sodium Starch Glycolate | 9.41% |
| 5% Polyvinylpyrrolidone in alcohol | q.s. |
| Talc | 1.176% |
| Magnesium stearate | 1.176% |

EXAMPLE 41

| | |
|---|---|
| Hydroalcoholic extract of the seeds of *Annona squamosa* | 11.11% |
| Aerosil | 38.88% |
| Lactose | 38.88% |
| Sodium Starch Glycolate | 8.88% |
| 5% Polyvinylpyrrolidone in alcohol | q.s. |
| Talc | 1.11% |
| Magnesium stearate | 1.11% |

EXAMPLE 42

| | |
|---|---|
| Hydroalcoholic extract of the seeds of *Annona squamosa* | 11.11% |
| Aerosil | 44.44% |
| Lactose | 33.33t% |
| Sodium Starch Glycolate | 8.88% |
| 5% Polyvinylpyrrolidone in alcohol | q.s. |
| Talc | 1.11% |
| Magnesium stearate | 1.11% |

EXAMPLE 43

| | |
|---|---|
| Hydroalcoholic extract of the seeds of *Annona squamosa* | 19.05% |
| Aerosil | 38.095% |
| Lactose | 33.33% |
| Sodium Starch Glycolate | 7.619% |
| 5% Polyvinylpyrrolidone in alcohol | q.s. |
| Talc | 0.952% |
| Magnesium stearate | 0.952% |

EXAMPLE 44

| | |
|---|---|
| Hydroalcoholic extract of the seeds of *Annona squamosa* | 20% |
| Aerosil | 40% |
| Lactose | 30% |
| Sodium Starch Glycolate | 8% |
| 5% Polyvinylpyrrolidone in alcohol | q.s. |
| Talc | 1% |
| Magnesium stearate | 1% |

EXAMPLE 45

| | |
|---|---|
| Hydroalcoholic extract of the seeds of *Annona squamosa* | 22.22% |
| Aerosil | 44.44% |
| Lactose | 22.22% |
| Sodium Starch Glycolate | 8.88% |
| 5% Polyvinylpyrrolidone in alcohol | q.s. |
| Talc | 1.11% |
| Magnesium stearate | 1.11% |

EXAMPLE 46

| | |
|---|---|
| Hydroalcoholic extract of the seeds of *Annona squamosa* | 25% |
| Aerosil | 50% |
| Lactose | 12.5% |
| Sodium Starch Glycolate | 10% |
| 5% Polyvinylpyrrolidone in alcohol | q.s. |
| Talc | 1.25% |
| Magnesium stearate | 1.25% |

EXAMPLE 47

| | |
|---|---|
| Hydroalcoholic extract of the seeds of *Annona squamosa* | 26.66% |
| Aerosil | 53.33% |
| Lactose | 6.66% |
| Sodium Starch Glycolate | 10.66% |
| 5% Polyvinylpyrrolidone in alcohol | q.s. |
| Talc | 1.33% |
| Magnesium stearate | 1.33% |

EXAMPLE 48

| | |
|---|---|
| Hydroalcoholic extract of the seeds of *Annona squamosa* | 35.29% |
| Aerosil | 47.058% |
| Lactose | 5.88% |
| Sodium Starch Glycolate | 9.41% |
| 5% Polyvinylpyrrolidone in alcohol | q.s. |
| Talc | 1.176% |
| Magnesium stearate | 1.176% |

The following in vitro tests were performed with the granules of the tablets of invention:

Bulk density:
Bulk density was found to be in the range of 0.40-0.42 g/cm$^3$

Tap density:
Tap density was found to be 0.42-0.425 g/cm$^3$ after 3 tappings and 0.460-0.465 g/cm$^3$ after 500 tappings.

Angle of repose:
Angle of repose was found to be in the range of 32-33°.
The following in vitro tests were performed with the tablets of invention:

Uniformity of weight:

The tablets complied with test for uniformity.

Hardness:

The hardness of the tablets was found to be in the range of 3-4 kg/cm$^2$ when tested using the Monsanto hardness tester.

Disintegration time:

The Disintegration time of the tablets ranged from 45 seconds to 1 minute.

Friability test:

The tablets complied with the U.S.P. requirements.

Spermicidal test:

Spermicidal activity of the tablets was carried out using the in vitro, Sander Crammer Immobilization test for determining the spermicidal activity.

Semen samples of healthy male volunteers were used for the study. The samples of motility more than 80% were used for the study. 10 µl of sperm suspension and 10 µl of the suspension obtained from the tablet after disintegration (1:1) were placed on a glass slide. Then it was mixed uniformly and examined under binocular microscope at a magnification of 10×. With the help of stopwatch, the time for the cessation of motility of spermatozoa was studied. The motility of the sperms was observed at different time intervals.

The spermicidal effect was found after 20 seconds of mixing. The partial immobilization began 1 minute after mixing the tablet with semen and spermicidal activity was found in 4-5 minutes depending on the vitality of the sperm.

Evaluation of antifertilty activity of vaginal tablets in rabbits:

The vaginal tablets were administered intravaginally to the female rabbits.

The females were allowed to mate with the male.

The females were then isolated.

Record the number of pregnancies after a period of one month.

The animals mated immediately after administration of the vaginal tablets. None of the female rabbits that were administered Annona vaginal tablets delivered while all rabbits which received the placebo tablets delivered pups. Thus Annona vaginal tablets showed 100% anti-fertility effect in vivo in rabbits.

While the present invention is described above in connection with preferred or illustrative embodiments, these embodiments are not intended to be exhaustive or limiting of the invention. Rather, the invention is intended to cover all alternatives, modifications and equivalents included within its spirit and scope, as defined by the appended claim.

We claim:

1. A stable non-synthetic herbal anti-fertility composition having a high spermicidal activity for intravaginal administration comprising a hydroalcoholic extract of seeds of *Annona squamosa*, said extract being present in an amount in the range of 1 wt. % to 80 wt. % of the total weight of composition, in combination with a mucoadhesive gel and pharmaceutically acceptable excipients.

2. The stable non-synthetic herbal anti-fertility composition according to claim 1, wherein said spermicidal activity is observed within a minimum period of 20-40 seconds.

3. The stable non-synthetic herbal anti-fertility composition according to claim 1, wherein the mucoadhesive gel is water washable.

4. The stable non-synthetic herbal anti-fertility composition according to claim 1, wherein the said composition comprises a mucoadhesive gel in the range of 0.5 wt. % to 30 wt. %.

5. The stable non-synthetic herbal anti-fertility composition according to claim 1, wherein the said mucoadhesive gel is selected from the group consisting of Carbopol, polycarbophil, xanthan gum, HPMC, sodium CMC, lutrol, carragenan, pemulen and pectin.

6. The stable non-synthetic herbal anti-fertility composition according to claim 1, wherein said composition further comprises sodium hydroxide.

7. The stable non-synthetic herbal anti-fertility composition according to claim 6, wherein the pH value of said gel is in the range of 4.5- 5.5.

8. The stable non-synthetic herbal anti-fertility composition according to claim 6, wherein said mucoadhesive gel may be used as lubricant in male and female condoms.

9. The stable non-synthetic herbal anti-fertility composition according to claim 1, wherein a process of preparing the composition comprises the steps of: a) soaking a gelling agent in water; b) extracting seeds of *Annona Squamosa* using a hydroalcohol to produce a hydroalcohol extract of *Annona squamosa*, c) concentrating the extract, and d) adding the hydroalcoholic extract of *Annona squamosa* to the soaked gelling agent; and c) optionally neutralizing using 10% NaOH.

* * * * *